US008647123B1

(12) United States Patent  
Carter et al.

(10) Patent No.: US 8,647,123 B1
(45) Date of Patent: Feb. 11, 2014

(54) FIRST RESPONDER EMERGENCY SITUATION ASSISTANCE DEVICE

(75) Inventors: Annette Carter, Cedar Rapids, IA (US); Paula Wickham, Cedar Rapids, IA (US); Kirk Dighton, Walker, IA (US); Troy Mundt, North Liberty, IA (US)

(73) Assignee: Retrac, Inc., Cedar Rapids, IA (US)

( * ) Notice: Subject to any disclaimer, the term of this patent is extended or adjusted under 35 U.S.C. 154(b) by 2293 days.

(21) Appl. No.: 11/160,245

(22) Filed: Jun. 15, 2005

(51) Int. Cl.
*G06F 15/00* (2006.01)

(52) U.S. Cl.
USPC .......................................... 434/262; 206/570

(58) Field of Classification Search
CPC ........................................................ G06F 15/00
USPC .......................................... 434/262; 206/570
See application file for complete search history.

(56) References Cited

U.S. PATENT DOCUMENTS

| 1,487,014 | A | * | 3/1924 | Davis ............................ 206/570 |
| 4,095,859 | A | * | 6/1978 | Decker et al. ................. 312/209 |
| 4,303,395 | A |   | 12/1981 | Bower |
| 4,513,866 | A |   | 4/1985 | Thomas |
| 4,824,376 | A | * | 4/1989 | Arash ........................... 434/330 |
| 5,042,116 | A | * | 8/1991 | Ossiani .......................... 24/303 |
| 5,086,391 | A |   | 2/1992 | Chambers |
| 5,088,037 | A | * | 2/1992 | Battaglia ....................... 600/300 |
| 5,515,974 | A | * | 5/1996 | Higson ......................... 206/570 |
| 5,521,812 | A |   | 5/1996 | Feder et al. |
| 5,644,294 | A | * | 7/1997 | Ness ............................. 340/540 |
| 5,668,954 | A |   | 9/1997 | Feder et al. |
| 5,848,700 | A |   | 12/1998 | Horn |
| 5,850,630 | A |   | 12/1998 | Wilson |
| 5,862,916 | A | * | 1/1999 | Utecht .......................... 206/570 |
| 5,931,304 | A | * | 8/1999 | Hammond .................... 206/570 |
| 6,210,329 | B1 | * | 4/2001 | Christmas et al. ............ 600/437 |
| 6,454,097 | B1 | * | 9/2002 | Blanco .......................... 206/570 |
| 6,460,702 | B2 |   | 10/2002 | Hammond |
| 6,758,811 | B1 |   | 7/2004 | Feder |
| 6,957,738 | B2 | * | 10/2005 | Hammond .................... 206/570 |
| 7,259,667 | B2 | * | 8/2007 | Sergio et al. ............. 340/539.11 |
| 2002/0078966 | A1 | * | 6/2002 | Lewis ........................... 128/897 |
| 2002/0104774 | A1 | * | 8/2002 | Hammond .................... 206/570 |
| 2003/0208357 | A1 |   | 11/2003 | Hammond |
| 2005/0015115 | A1 |   | 1/2005 | Sullivan et al. |

* cited by examiner

*Primary Examiner* — Xuan Thai
*Assistant Examiner* — Alvin Carlos
(74) *Attorney, Agent, or Firm* — Zarley Law Firm, P.L.C.

(57) ABSTRACT

The present invention is a first aid emergency supply kit capable of providing audio and/or video instructions to the user as to how to use the medical supplies contained in the kit. The case is organized so that the medical supplies for different traumas are packaged into individual bags. The user can activate the audio and/or video instructions by pushing a button on the unit's console that corresponds to the particular trauma. Alternatively, the instructions can be activated by removing a bag from the case which automatically begins the instructions. If a victim has sustained multiple injuries, and the user has depressed multiple buttons or removed multiple bags, then the device automatically prioritizes the traumas and provides instructions on the multiple traumas in the proper order.

18 Claims, 6 Drawing Sheets

FIRST RESPONDER EMERGENCY SITUATION ASSISTANCE DEVICE

BACKGROUND OF THE INVENTION

In the United States there were over 27,000,000 nonfatal injuries reported as being treated by hospital emergency departments in 2002. The National Safety Council statistics showed 20,400,000 unintentional disability injuries and 99,500 unintentional deaths in the U.S. for that same year. For each of these traumas there is a period of time known as a "gap." The gap is that period of time where family, coworkers, or other bystanders with little or no medical training are at the scene of an accident attempting to assist the victim. A national standard shows the average urban response time (the gap) for advanced care is 8.5 minutes. Rural response times have not been established, but they are suspected to be somewhat longer than the average urban response time.

The gap is the most important time period in which to prevent further damage to the victim and help to preserve a victim's life. Victims who receive definitive, necessary and proper care in airway management, choking, bleeding, and management of burns within the first five minutes of injury are more likely to have minimal damage. In some cases, incorrect assistance can cause more damage to the victim than no assistance at all. Thus, an individual at the scene of an accident with limited knowledge and resources makes crucial decisions that can positively or negatively affect human life.

The American Red Cross has identified that even people who have taken first aid classes may not remember what to do in an emergency situation. Their studies have shown that the retention rate of the skills covered in a first aid class decreases after six weeks and is likely gone after six months. This lack of retention is magnified when the stress and panic of an actual trauma is presented. It is therefore crucial that the person administering the assistance stay calm so as to better remember what steps to take to help the victim.

Traditional first responder kits are inefficient for several reasons. First, traditional kits provide supplies with only written instructions on their usage. This can either increase the time it takes for the person to provide assistance to the victim, or it can lead to incorrect assistance if the person decides not to read the instructions before administering assistance. Second, traditional kits do not organize supplies by type of trauma, rather, they package supplies together with like supplies. For example, rubber gloves and band-aids are packaged together with various sized gloves and assorted band-aids even thought the entire box will not be used during one trauma. This packaging system can add to confusion for the person administering the first aid because the person may not remember what supplies or medications should be used to treat the trauma. Finally, traditional kits do not assist in helping to calm the person administering the aid or provide immediate prompting as to how to address the trauma situation or multiple situations. This can lead to incorrect actions by the person administering the first-aid or it may decrease the chances that a bystander will remember what to do for the trauma situation.

There are several known devices which are directed toward first aid kits. These devices include U.S. patent application Ser. No. 10/140,462 and U.S. Pat. Nos. 5,850,630 and 6,460,702. Some of these devices disclose a means for providing audio instructions to the care giver which help the care giver remember how to provide assistance to victims in certain trauma situations. The problem with these devices is that they do not offer the ability to prioritize which trauma is most important when the victim has sustained multiple traumas. In other words, an inexperienced care giver may tell the device to give instructions for bleeding when proper medical procedure would actually call for the care giver to be doing CPR on the victim first. Further, the devices disclosed in these patents are inefficient because they require the user to turn them on and then correctly select the instructions for the appropriate trauma. In the stress of an emergency situation, it is likely that the user will make a mistake and incorrectly press buttons on the console, which can cause more harm to the victim because more time passes before the first aid is administered.

Therefore, there is a need for a medical supply kit that is able to help laypersons calmly and efficiently provide assistance to a victim in an emergency situation and prioritizes the severity of the victim's traumas in a multiple trauma situation.

SUMMARY OF THE INVENTION

The present invention is a first-aid emergency supply kit adapted to provide audio and/or video instructions to the user as to how to use the medical supplies contained in the kit. The kit comprises a case which contains a plurality of bags carried by the case. Each bag contains medical supplies aimed at addressing one particular type of trauma situation. Each bag is comprised of a unique color and number allowing for quick reference, as is further described below. A brief description of the trauma that the supplies in the bag are aimed at addressing is printed on the outside of the bag.

The kit further comprises a console having a plurality of buttons and other types of switches for controlling the audio and/or video instructions. The color, number, and printed trauma description on each bag corresponds to the color, number, and trauma description associated with one of the buttons on the unit's console. As indicated above, the programmed instructions can be audio, visual, or both. Pressing one of the buttons begins the instructions for treating the trauma indicated by that button. If the user pushes multiple buttons, thereby signifying that the victim has sustained multiple traumas, the device prioritizes the traumas and gives instructions in the order that the traumas should properly be addressed according to standard medical procedures and protocols, regardless of the order in which the user pressed the buttons. The buttons on the console allow the user to skip forward, pause, rewind, and otherwise efficiently navigate the audio and/or video instructions in the event of a mistakenly pressed button or other reason for navigation.

In addition to or as an alternative to pressing a button to begin the instructions, the audio and/or video instructions can be activated by simply opening or removing a bag from the case. In this embodiment, the bags are connected to the case in such a manner that removing a bag from the case automatically begins the audio and/or video instructions for the trauma associated with the removed bag(s). This reduces the amount of time the user spends determining which button(s) to push and allows the user to immediately obtain the necessary supplies contained in the removed supply bag. If multiple bags are removed, thereby signifying that the victim has sustained multiple traumas, the device prioritizes the traumas and gives instructions in the order that the traumas should properly be addressed according to standard medical procedures and protocols, regardless of the order in which bags were removed.

In addition to audio and/or video instructions, the case includes a first-aid instruction booklet and an overview card for each bag. It should be noted that the printed instructions will typically not be used in an emergency situation unless the audio/video instruction system fails. The overview card is color coded and numbered so as to correspond with the appropriate bag and console button. The instruction booklet has tabs that are color coded and numbered so as to correspond with the bags, buttons, and overview cards. The instruction booklet and/or overview cards have instructions and illustrations on how to address trauma situations, such as diagrams that show where to apply CPR compressions on a person's chest.

The audio and/or video instructions guide inexperienced persons or out-of-practice first responders through the treatment of a multiple injury trauma so as to address the situation in a calm and proper manner. The benefit of the invention is that the device allows for prompt audible instructions that address a situation or addresses and prioritizes multiple situations. The user can listen to the instructions without having to take time to read anything so as to more quickly assess an urgent situation and address it. An additional advantage is that the case can be easily re-stocked by simply re-stocking the particular bag(s) that was needed to address the trauma. This increases efficiency and decreases waste by allowing the user to re-stock only the medical supplies that have been used instead of having to purchase an entirely new first-aid kit to replace only a few medical items.

This device provides confidence and comfort for businesses, families, and individuals who may be confronted with an unexpected emergency. The device provides the victim with immediate and efficient care during the gap period and thus provides a better chance of survival and less chance of disability for the victim.

DESCRIPTION OF THE PREFERRED EMBODIMENT OF THE INVENTION

The present invention is a self contained emergency supply kit capable of providing audio and/or video instructions to the user as to how to use the medical supplies contained in the kit. It should be noted that although the majority of this specification describes the invention as a first-aid tool, the kit can be used for any suitable application including as a pediatric or advanced medical assistance kit, wilderness survival kit, or earthquake survival kit. Examples of the types of traumas that the kit may address include CPR, choking, bleeding, head/spine injuries, eye injuries, cardiac, seizure, radiation poisoning, fractures/sprains, burns, poisoning, and heat stress.

Figure 1:
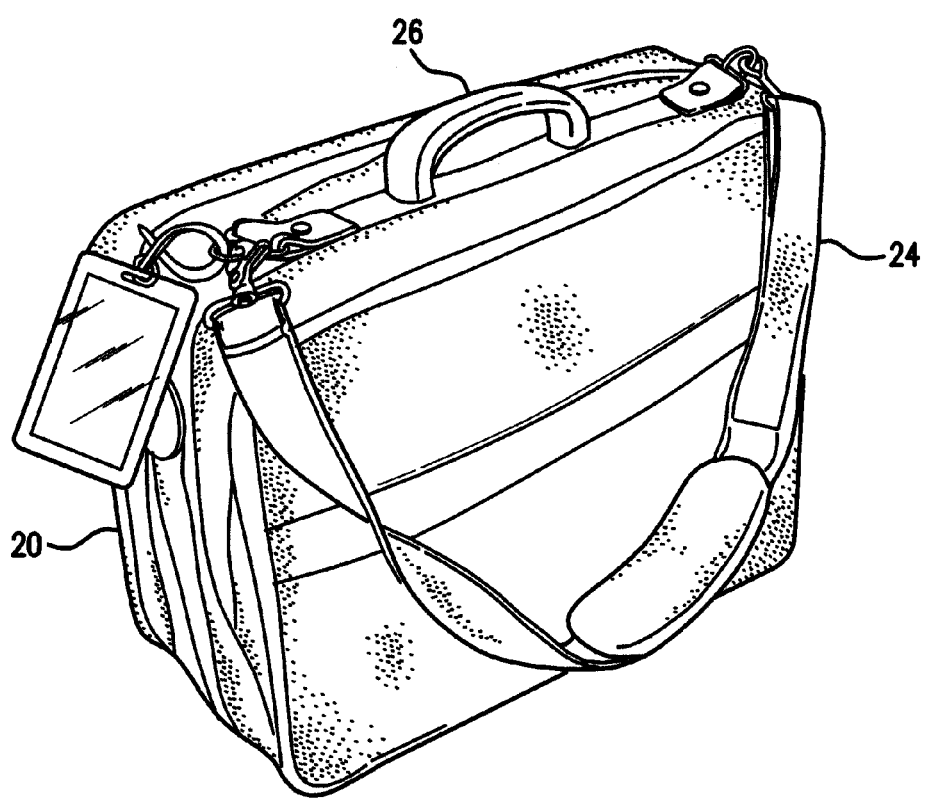
FIG. 1 is a perspective view of the present invention showing the case in the closed position.
Figure 2:
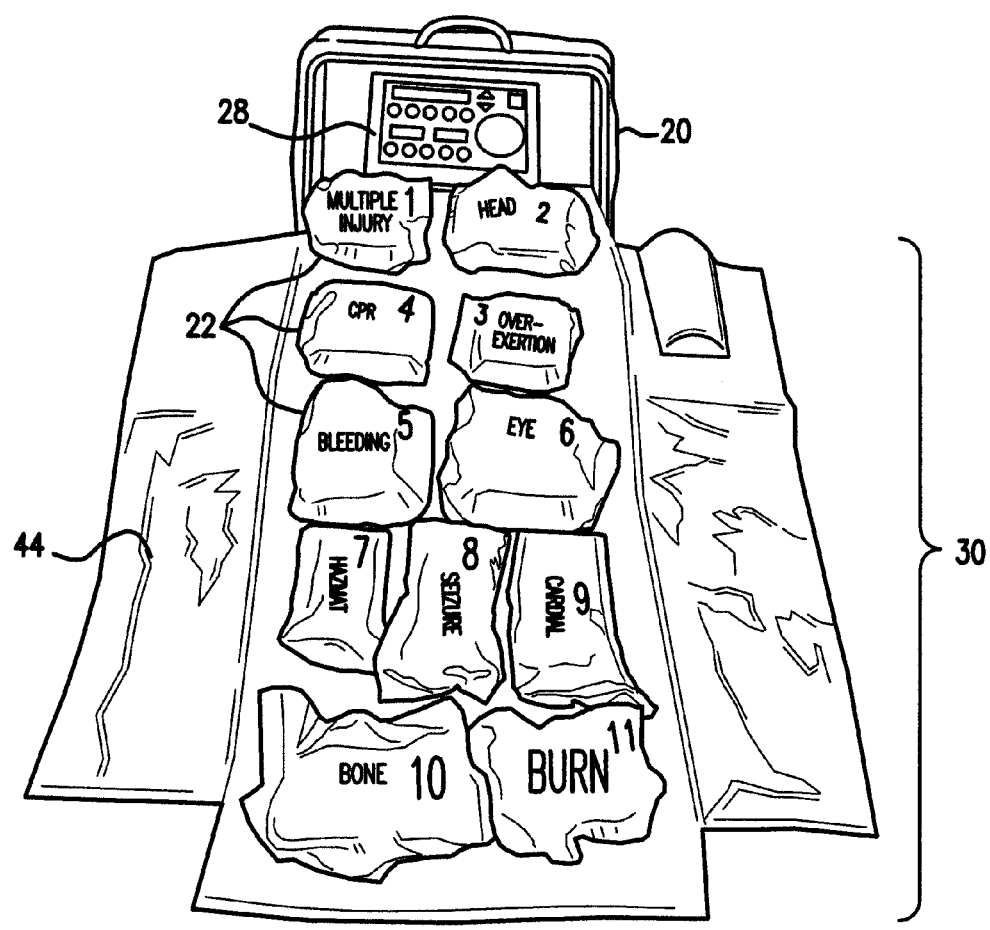
FIG. 2 is a perspective view of the present invention showing the case in the open position and the break-away bags containing the medical supplies.

As shown in FIGS. 1 and 2, the kit comprises a case 20 having a plurality of bags 22 containing medical supplies. The bags 22 are attached to the case 20 in a roll-out fashion, as is further described below. The case 20 can be opened and closed using a zipper or any other suitable means so as to protect the contents of the case 20 when the case 20 is closed and not in use. The case 20 preferably has a handle 26 and a shoulder strap 24 to aid in carrying it. Additional medical supplies not contained in the individual bags 22 may be contained in the top, bottom, or sides of the case 20. Preferably, the case 20 has an inspection tag adapted to allow users to declare and sign off as to when the kit was last inspected and stocked.

Each of the plurality of bags 22 contain medical supplies adapted for treating one particular kind trauma. Each bag 22 is a different color and has a different number printed on it to allow for quick reference. A brief description of the trauma that the supplies in each bag 22 addresses is printed on the outside of the bags 22. Preferably, as shown in FIG. 2, the bags 22 are combined with a portion of the case 20 referred to as the roll out portion 30. The roll out portion 30 rolls up for storage in the case 20 when the case 20 is in the closed position, and quickly rolls out to display the bags 22 when the case 20 is in the open position. In its extended position, the roll out portion 30 allows the user to quickly see all of the bags 22 contained in the case 20 without having to open additional pouches or dig through other supplies that may be contained in the case 20. The bags 22 are combined with the roll out portion 30 in such a manner that they can be easily detached from the roll out portion 30. As seen in FIG. 2, the roll out portion 30 preferably has flaps 44 to help contain and protect the bags 22 when the device is not in use. The roll out portion 30 of the case 20 is preferably detachable from the case 20 for cleaning purposes and preferably made of a fabric such as nylon so that it is durable yet flexible.

Figure 3:
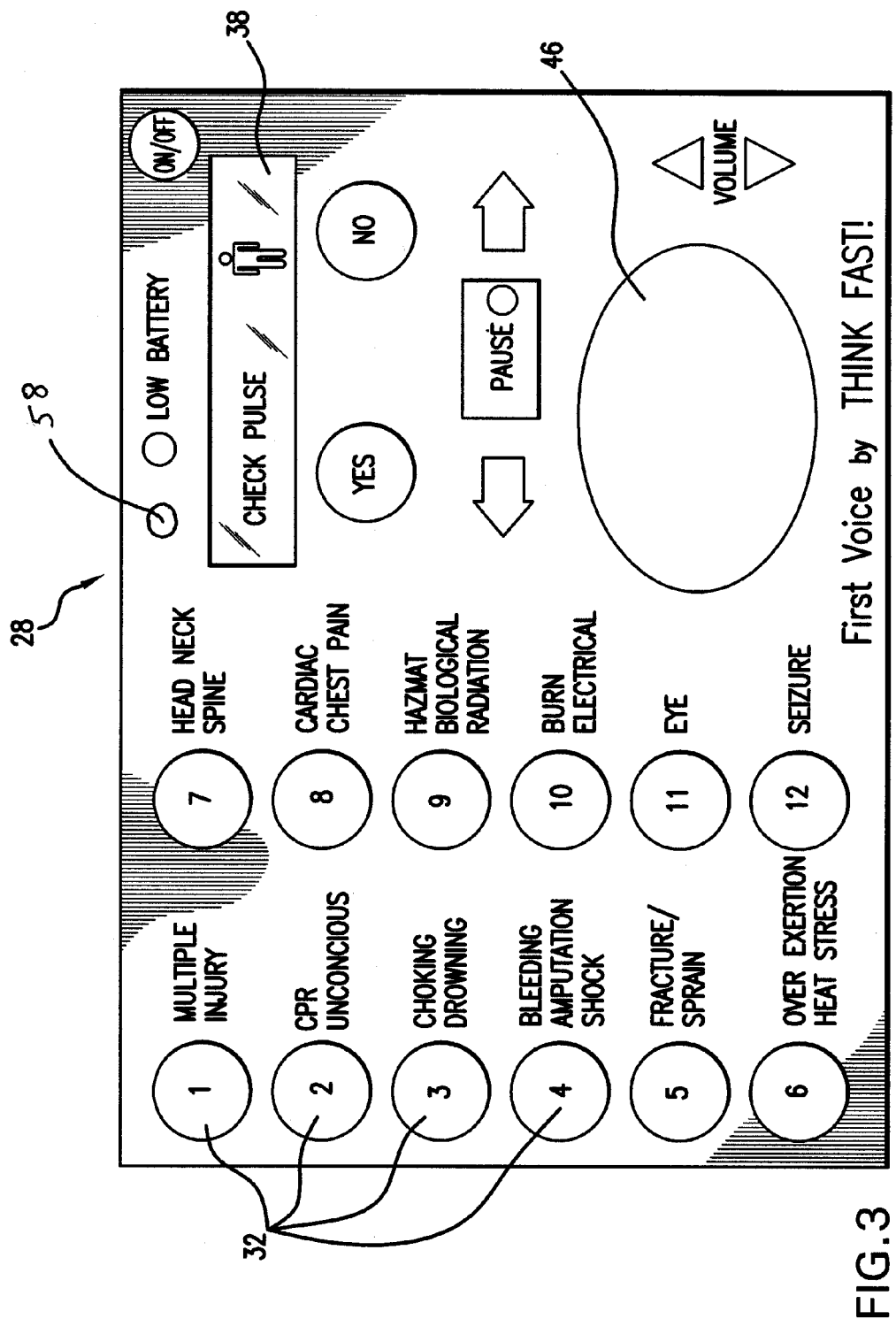
FIG. 3 is a perspective view of the case's console.

As shown in FIGS. 2 and 3, the kit further comprises a console 28. In the preferred embodiment, the console 28 is removable from the case 20 so that the user can easily position it in a convenient location when receiving and navigating the instructions and administering assistance to the victim. The console 28 has a plurality of switches for controlling the circuitry related to the audio and/or video instructions. The switches can be buttons, levers, knobs, or any other suitable means for providing signals to the circuitry of the device. The switches may control functions such as volume, pause, rewind, restart, power, skip ahead, language selection, and any other suitable function that allows the user to efficiently navigate the audio and/or video instructions. Some of the switches have a color, number, and trauma description associated with them that correspond with a bag 22 having the same color, number, and description. These switches are called task selection keys 32, which are further described below. In the preferred embodiment, the console 28 also comprises "yes" and no switches which aid the user in the navigation of the audio and/or video instructions. For example, the audio instructions may ask the user if the bleeding has stopped, to which the user would press either the "yes" or no switch which would prompt the device as to which set of pre-recorded instructions to provide to the user. In an alternate embodiment, the kit may comprise voice recognition software that allows the device to respond to verbal commands given by the user. This embodiment would improve the speed and efficiency with which a user could provide first-aid treatment to a victim because the user would not have to spend time pressing the various switches, instead, the user would only have to verbally speak the commands to the device.

Figure 6:
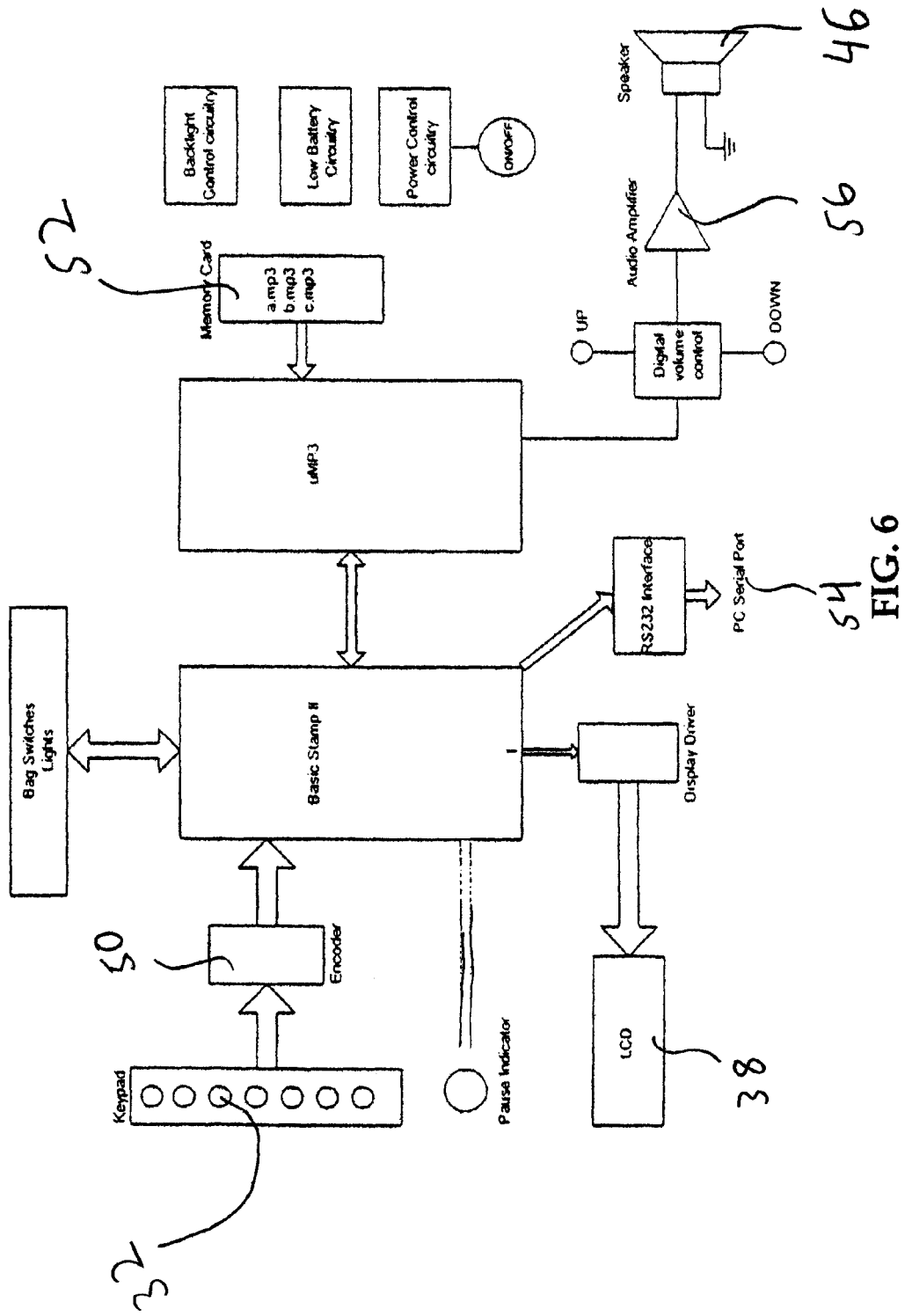
FIG. 6 is a diagram of the circuitry for the electronic automated voice unit.

FIG. 6 shows a schematic of the circuitry of the kit. Among other things, FIG. 6 shows that the invention comprises a voice unit which has a means for providing audible instructions to the user. The voice unit includes a speaker 46 mounted in the console 28 for projecting the audible instructions and a memory for storing the instructions in electronic format. The audible instructions can be activated by one of several ways. First, the instructions can be activated by pushing one or more of the plurality of color coded and numbered task selection keys 32 on the console 28. All color coded and numbered task selection keys 32 correlate to the colored and numbered bags 22 attached to the case 20. The bag 22 that corresponds to the task selection key 32 contains medical supplies aimed at treating the indicated trauma. As seen in FIGS. 2 and 3, both the keys 32 and the bag 22 have a description of the trauma printed on them.

Figure 4:
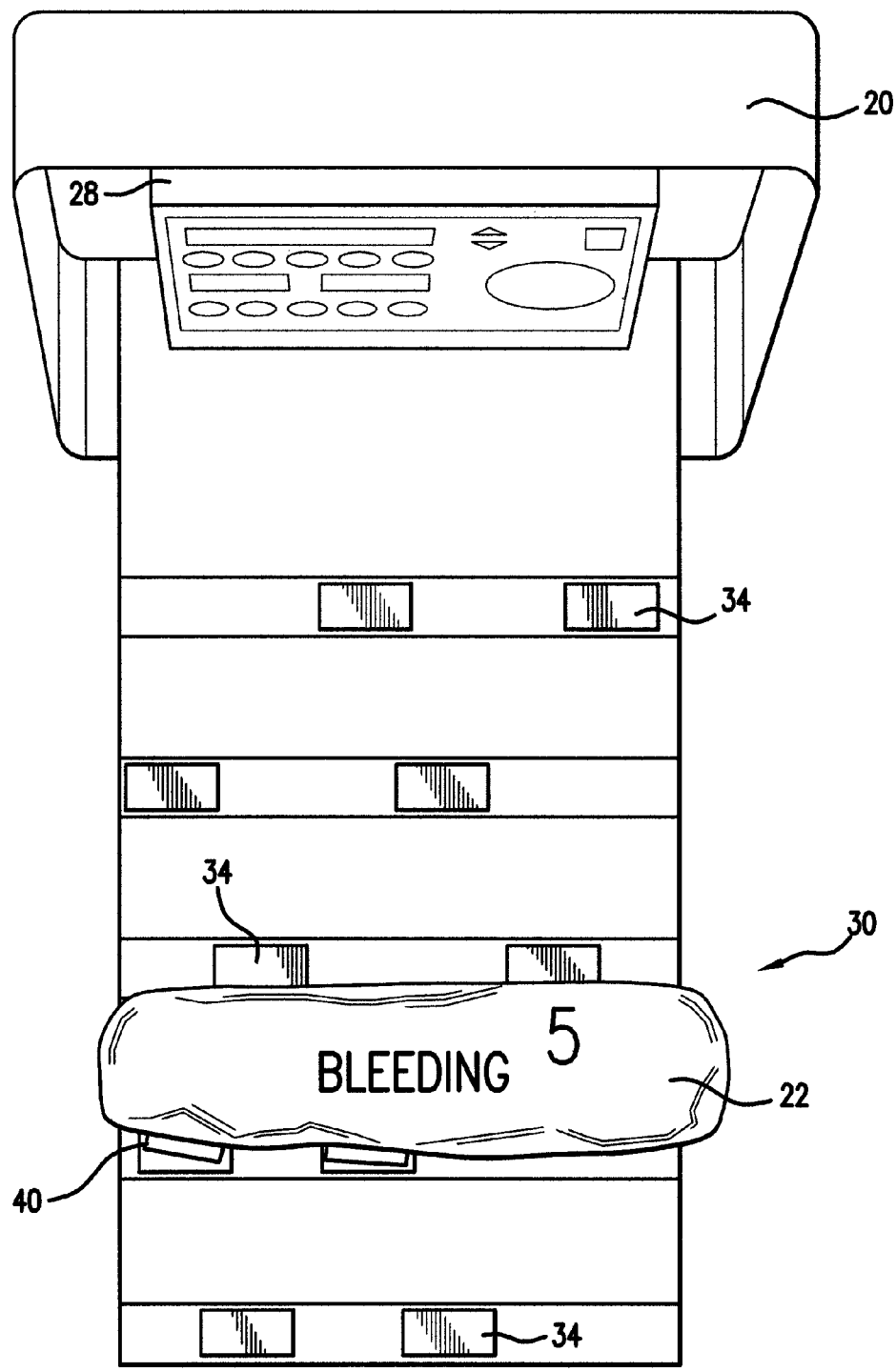
FIG. 4 is a top view showing the connection points on the roll out portion of the case which combined with the break-away bags.

In an alternate embodiment shown in FIG. 4, the bags 22 are combined with the roll out portion 30 of the case 20 by a connector. In the preferred embodiment the connector is an electronic switch 34 means which triggers the audio/video instructions when a bag 22 is removed from the case 20. The term for the bags 22 in this embodiment is "break away" bags 22 since breaking them away from the case 20 automatically triggers the start of the instructions.

In this embodiment, the switch 34 used to trigger the break away bags 22 is preferably a magnetic switch 34. A magnet(s) 40 is combined with the bag 22 and a magnetic switch 34 is combined with the roll out portion 30 of the case 20. When the magnet 40 on the bag 22 is no longer in close proximity to the switch 34, an electronic signal tells the device that the bag 22 has been removed. The device then begins the instruction sequence for the trauma associated with the removed bag 22. As seen in FIG. 4, the positioning of the switches 34 and corresponding magnets 40 on each bag 22 is unique so that each bag 22 can only be combined with the roll out portion 30 in one location. This prevents bags 22 from being attached to the wrong location on the roll out portion 30 which could result in the wrong instructions being given for a particular bag 22. When the bags 22 are all combined with the roll out portion 30, or when power is first applied, the device will automatically check to determine whether all bags 22 are in their proper location on the roll out portion 30. The device will indicate to the user whether the bags 22 are correct, or whether a bag 22 is incorrect or missing.

As discussed above, pressing one of the keys 32 or removing one of the break-away bags 22 begins the instructions for treating the indicated trauma. If the user pushes multiple keys 32 or removes multiple bags 22, thereby signifying that the victim has sustained multiple traumas, the device will prioritize the traumas and give instructions in the order that the traumas should properly be addressed according to standard medical procedures or protocols for emergency/pre-hospital medical care, regardless of the order in which the user pressed the keys 32 or removed the bags 22. Once the pertinent bags 22 have been pulled from the unit (or keys 32 have been pushed), indicating a multiple injury situation, the priority rules which have been established by standard medical procedures and programmed into the circuitry of the device give instructions on the most urgent situation first. In instances where it is hard to assess which injury is more urgent, the device will prompt the user as to which trauma to address first using a series of stored "yes" or "no" questions to which the user will respond using the "yes" and no buttons on the console 28. The device contains software adapted to prioritize instructions obtained from a programmed predetermined set of rules based on bag 22/selection key 32 input as well as the "yes"/"no" input provided by the user.

The electronic automated voice unit is the preferred means for communicating instructions to the user as discussed above, however; there are several other means for communicating instructions to the user. As shown in FIG. 3, the instructions may be presented in video format, either using pictures or printed language on a video display screen 38. In this video embodiment, the console 28 of the device preferably has a liquid crystal display (LCD) or video display 38 that, among other things, reminds the user to continually assess the vital signs of the victim as a means of trying to decrease victim fatality or disability due to addressing one emergency situation but forgetting to re-assess vital signs (breathing, pulse, etc. . . . ) while completely addressing the one situation. The video display 38 can also provide abbreviated visual instructions using words or pictures. For example, the video screen 38 may show a diagram of a human body with arrows pointing to the proper location of applying chest compressions when administering CPR. The video instructions may be activated and navigated in the same manner as the audio instructions discussed above.

The audio and/or video components of the present invention are powered by a power supply contained in the case. In the preferred embodiment, the power supply is a battery pack that may be rechargeable. The audio instructions are preferably stored on an embedded MP3 player to play voice files which are stored under an MP3 format. This is shown in FIG. 6 which shows the preferred circuitry for the device. The MP3 format files will be played via the assistance of a microcontroller and an encoder 50. The unit will preferably employ a removable flash memory card 52 to store voice files or other means for storing memory and allow for ease of file updates using a USB port or other port 54. The microcontroller will receive inputs on which voice file or software code/script to play or what action to take from the console 28/keypad buttons 32 on the device or via the switches 34 from roll out portion 30 of the bag 20. Once the microcontroller identifies from the keypad or switches 34 the proper voice files or software code to play, it is played via the assistance of an audio amplifier 56 and outputs to a speaker 46. The speaker 46 volume is controlled via volume keys on the console 28 of the device. The microcontroller also drives the video display 38. Proper visual instructions are played on the video display 38 with the assistance of the display driver. The visual instructions are displayed after the microcontroller identifies from the console 28 or the switches 34 which instructions or coding are to be played/shown in conjunction with the proper voice instruction from the speaker 46 output.

In the preferred embodiment, the device has several features that add to the efficiency and reliability of the device. First, the device preferably is adapted to receive an ear plug or head phone jack that allows the user to hear the audio instructions more easily in a loud environment such as a factory. Second, the device preferably has a low battery indicator light which will flash and prompt a loud beeping sound from the case to indicate that the batteries need to be replaced. Third, the device preferably has an auto shutoff feature that turns the device off if the unit has not been used after a predetermined amount of time. Fourth, the device preferably has a global positioning system (GPS) transmitter enclosed which enables emergency services to pinpoint the location of the device and more easily be directed to the victim. The GPS transmitter can be activated either automatically, or when the user pushes a designated button 58 on the console 28. Fifth, the device may include a transmitter which is adapted to call emergency services, such as 911, either automatically or when the user pushes a designated button on the console 28. Finally, the device preferably has the capability to allow for a USB port or other port to allow for downloading new or updated information or software upgrade into the unit in the future. FIG. 6 shows a PC serial port which allows for updated information or updated/amended software code to be stored on the microcontroller for future use by the electronic unit.

The case 20 also may include several "upgradeable" supplies stored in various portions of the case 20. These supplies can help an experienced first responder from a specific market address specific hazards related to their duties in industry, fire, EMT, CERTS, and other first responder areas. For example, a fire blanket may be contained in the case 20 that is used by fire first responders. The case 20 also may contain extra supply bags which contain a plurality of extra supplies in the event that more supplies are needed to address an emergency situation. The extra bags 22 may also contain non-disposable items that do not need to be disposed of after treating a victim, such as scissors, tweezers, or tape.

Figure 5:
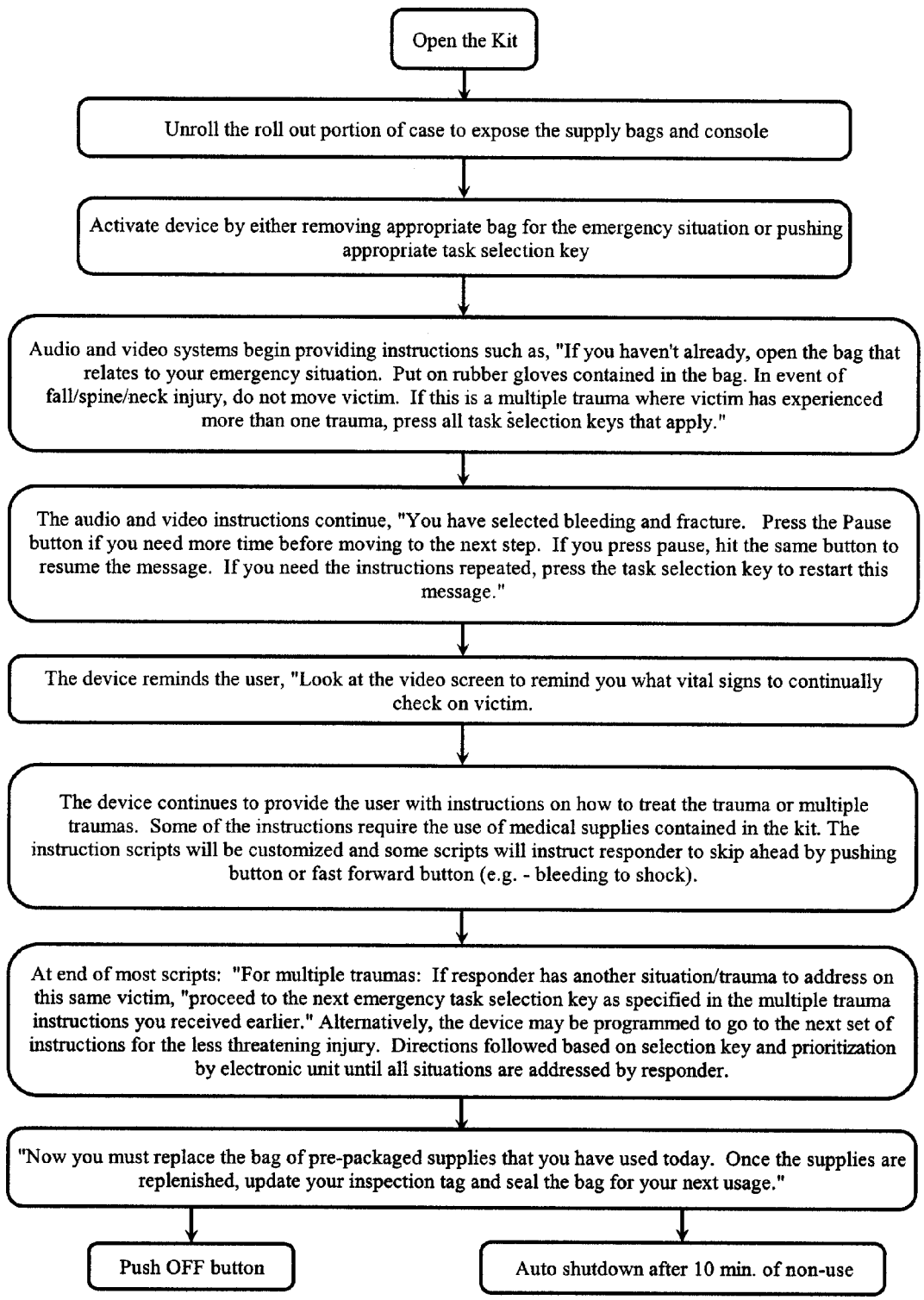
FIG. 5 is a flow chart showing exemplary general steps and possible instructional language used with the device.

FIG. 5 shows a flow chart for an exemplary use of the device. In use, the case 20 will be opened after a trauma has occurred. The user will either press one or more of the keys 32 or remove one or more of the break-away bags 22 to begin the programmed instructions. If more than one button 32 is pushed or more than one bag 22 is removed, the device will automatically prioritize the traumas and provide instructions in the proper order according to current medical standards, regardless of the order in which the keys 32 were pushed or bags 22 removed by the user. The user will open the selected bag 22 or bags and remove the medical supplies contained therein. The audio and/or video instructions will guide the user in properly treating the victim. The user can skip ahead, pause, or rewind portions of the instructions as the individual situation dictates. After an emergency response team has arrived and taken over care of the victim, the user can easily restock the supplies used by replacing the individual bags 22 used in treating the victim. The kit can be sealed with a plastic seal/inspection tag after restocking to show proper supplies are once again self-contained and to prevent confusion or harm caused by an unknown lack of emergency supplies contained in the kit.

Having thus described the invention in connection with the preferred embodiments thereof, it will be evident to those skilled in the art that various revisions can be made to the preferred embodiments described herein with out departing from the spirit and scope of the invention. It is my intention, however, that all such revisions and modifications that are evident to those skilled in the art will be included with in the scope of the following claims.

What is claimed is:

1. An instructional medical supply device adapted to provide instructions to a user for carrying out a plurality of medical emergency related tasks when a user activates the instructions associated with one or more of the tasks, said medical supply device comprising:
   a case having an open position and a closed position;
   a plurality of bags carried by the case when the case is in the closed position, each bag containing supplies adapted for addressing at least one of said plurality of medical tasks;
   a console combined with the case, the console having a plurality of task selection keys, each task selection key relating to at least one of said plurality of medical tasks;
   circuitry and software in communication with the console, said circuitry and software adapted to store and communicate the instructions to the user;
   a speaker in communication with the circuitry, said speaker adapted to audibly output the instructions for at least one of said tasks;
   a power supply in communication with the circuitry for powering the device; wherein the device has a power-off state and a power-on state and removal of one of the bags from the case causes the device to be in the power-on state; and wherein when in a power-on state the circuitry and the software of the device are adapted to prioritize the traumas selected by the user in accordance with standard medical procedures and provide the user with instructions as to the selected tasks in the proper order regardless of the order in which the user selected the tasks.

2. The device of claim 1 wherein activation of one of the task selection keys begins the instructions for the task related to that selection key.

3. The device of claim 1 wherein the console is removable from the case.

4. The device of claim 1 wherein the data is stored in the software in MP3 format.

5. The device of claim 1 further comprising a video screen for providing visual instructions to the user relating to the medical tasks.

6. The device of claim 1 wherein the console further comprises "yes" and "no" keys in communication with the circuitry and the software, said keys adapted to allow the user to navigate the instructions by responding to predetermined questions stored by the device.

7. The device of claim 1 further comprising a global positioning system transmitter adapted to broadcast a signal to allow emergency services to pinpoint the location of the device.

8. The device of claim 1 further comprising a transmitter adapted to call emergency services via telephone.

9. The device of claim 1 wherein the software comprises voice recognition software adapted to allow the device to recognize verbal commands given by the user.

10. An instructional medical supply device adapted to provide instructions to a user for carrying out a plurality of medical emergency related tasks, said medical supply kit comprising:
    a case having an open position and a closed position;
    a plurality of bags combined with the case, each bag containing supplies adapted for addressing at least one of said plurality of medical tasks;
    circuitry and software adapted to store and play the instructions;
    a speaker in communication with the circuitry, said speaker adapted to audibly output instructional data concerning at least one of said tasks;
    a power supply in communication with the circuitry for powering the device;
    wherein the device has a power-off state and a power-on state in which the device begins giving instructions to the user, and removal of one of the bags from the case causes the device to be in the power-on state without the operation of a dedicated power switch.

11. The device of claim 10 wherein the case further comprises a roll out portion, and the bags are removably combined with the roll out portion of the case by a connector.

12. The device of claim 11 wherein the connector is a magnet.

13. The device of claim 11 wherein the connector is a magnet and a magnetic switch is combined with the roll out portion of the case.

14. The device of claim 11 wherein the placement of the connector is positioned relative to each bag so that the bags cannot be combined incorrectly with the roll out portion.

15. The device of claim 10 wherein the roll out portion is detachable from the case for cleaning purposes.

16. The device of claim 10 further comprising a console combined with the case, the console having a plurality of task selection keys.

17. The device of claim 16 wherein activation of one of the task selection keys begins the instructions for the task related to that selection key.

18. An instructional medical supply device configured to provide medical condition specific instructions to a user for carrying out a plurality of medical emergency related tasks when a user activates instructions associated with one or more of a plurality of predefined medical conditions, said medical supply device comprising:

a case having an open position and a closed position;

said case comprising a roll-out portion having detachably disposed thereon a plurality of bags, each bag containing supplies preselected for addressing and a label for describing one of said plurality of predefined medical conditions;

said plurality of bags each being magnetically coupled to a portion of the case such that when any of said plurality of bags is detached from said case, an electronic signal is provided to circuitry and software coupled with the console so as to enable identification of which bag has been detached and which predefined medical condition is associated with any such detached bag;

a console disposed within the case, the console having a plurality of selection keys, each selection key relating to at least one of said plurality of predefined medical conditions;

circuitry and software coupled with the console, said circuitry and software configured to store and play the medical condition specific instructions;

a speaker in communication with the circuitry, said speaker configured to audibly output the instructions for at least one of said tasks; and a power supply coupled with the circuitry for powering the device;

said circuitry and software further configured to prioritize medical condition specific instructions if more than one bag of said plurality of bags is detached from the case, where prioritization of medical condition specific instructions is done in accordance with predetermined standard medical procedures; and a power-on state of said device is automatically accomplished when a first of said plurality of bags is detached from the case.

\* \* \* \* \*